US012283196B2

(12) United States Patent
Jin et al.

(10) Patent No.: US 12,283,196 B2
(45) Date of Patent: Apr. 22, 2025

(54) SURGICAL SIMULATOR PROVIDING LABELED DATA

(71) Applicant: Verily Life Sciences LLC, South San Francisco, CA (US)

(72) Inventors: Xing Jin, San Jose, CA (US); Joëlle K. Barral, Mountain View, CA (US); Lin Yang, Sunnyvale, CA (US); Martin Habbecke, Palo Alto, CA (US); Gianni Campion, Mountain View, CA (US)

(73) Assignee: Verily Life Sciences LLC, Dallas, TX (US)

( * ) Notice: Subject to any disclaimer, the term of this patent is extended or adjusted under 35 U.S.C. 154(b) by 588 days.

(21) Appl. No.: 17/552,886

(22) Filed: Dec. 16, 2021

(65) Prior Publication Data

US 2022/0108450 A1 Apr. 7, 2022

Related U.S. Application Data

(63) Continuation of application No. 16/373,261, filed on Apr. 2, 2019, now Pat. No. 11,232,556.

(Continued)

(51) Int. Cl.
*G09B 23/28* (2006.01)
*G06N 3/08* (2023.01)
(Continued)

(52) U.S. Cl.
CPC .............. *G09B 23/28* (2013.01); *G06N 3/08* (2013.01); *G06T 7/0012* (2013.01);
(Continued)

(58) Field of Classification Search
CPC ......... G06T 7/0012; G06T 2207/30004; G06T 2207/20084; G06T 2207/20081;
(Continued)

(56) References Cited

U.S. PATENT DOCUMENTS 9,700,292 B2 7/2017 Nawana et al.
10,679,046 B1 * 6/2020 Black ..................... G06V 40/23
(Continued)

FOREIGN PATENT DOCUMENTS

WO 2017/083768 A1 5/2017

OTHER PUBLICATIONS

Shrivastava, Ashish, et al. "Learning from Simulated and Unsupervised Images through Adversarial Training." 2017 IEEE Conference on Computer Vision and Pattern Recognition (CVPR). IEEE, 2017 (Year: 2017).*

(Continued)

*Primary Examiner* — Leon Viet Q Nguyen
(74) *Attorney, Agent, or Firm* — Christensen O'Connor Johnson Kindness PLLC (57) ABSTRACT

A surgical simulator for simulating a surgical scenario comprises a display system, a user interface, and a controller. The controller includes one or more processors coupled to memory that stores instructions that when executed cause the system to perform operations. The operations include generating simulated surgical videos, each representative of the surgical scenario. The operations further include associating simulated ground truth data from the simulation with the simulated surgical videos. The ground truth data corresponds to context information of at least one of a simulated surgical instrument, a simulated anatomical region, a simulated surgical task, or a simulated action. The operations further include annotating features of the simulated surgical videos based, at least in part, on the simulated ground truth data for training a machine learning model.

13 Claims, 5 Drawing Sheets

Related U.S. Application Data (60) Provisional application No. 62/660,726, filed on Apr. 20, 2018.

(51) Int. Cl.
*G06T 7/00* (2017.01)
*G06V 10/44* (2022.01)
*G06V 10/75* (2022.01)
*G06V 10/764* (2022.01)
*G06V 10/82* (2022.01)
*G06V 20/20* (2022.01)
*G06V 20/40* (2022.01)

(52) U.S. Cl.
CPC .......... *G06V 10/454* (2022.01); *G06V 10/751* (2022.01); *G06V 10/764* (2022.01); *G06V 10/82* (2022.01); *G06V 20/20* (2022.01); *G06V 20/41* (2022.01); *G06T 2207/20081* (2013.01); *G06T 2207/20084* (2013.01); *G06T 2207/30004* (2013.01)

(58) Field of Classification Search
CPC .... G06N 3/08; G06N 3/0454; G06K 9/00718; G06K 2209/057; G06K 9/00671; G06K 2209/05; G06K 9/4628; G06K 9/6202; G06K 9/6274; A61B 2034/2055; A61B 2034/101; G09B 23/28
USPC ................................. 382/155–160
See application file for complete search history.

(56) References Cited

U.S. PATENT DOCUMENTS

| | | | |
|---|---|---|---|
| 11,232,556 B2 * | 1/2022 | Jin | G06V 10/764 |
| 2009/0263775 A1 | 10/2009 | Ullrich | |
| 2018/0357514 A1 * | 12/2018 | Zisimopoulos | G06V 10/764 |

OTHER PUBLICATIONS

Twinanda, Andru P., et al. "Endonet: a deep architecture for recognition tasks on laparoscopic videos." IEEE transactions on medical imaging 36.1 (2016): 86-97 (Year: 2016).*

Gillan, Stewart N., and George M. Saleh. "Ophthalmic surgical simulation: a new era." JAMA ophthalmology 131.12 (2013): 1623-1624 (Year: 2013).*

Bousmalis, K., et al., "Unsupervised Pixel-Level Domain Adaptation with Generative Adversarial Networks," Dec. 16, 2016, Arxiv.org, Cornell University Library, Cornell University, Ithaca, New York, 16 pages.

International Search Report and Written Opinion mailed Jul. 9, 2019, issued in corresponding International Application No. PCT/US2019/028389, filed Apr. 19, 2019, 12 pages.

Johnson-Roberson, M., et al., "Driving in the Matrix: Can Virtual Worlds Replace Human-Generated Annotations for Real World Tasks?" Proceedings of the 2017 IEEE International Conference on Robotics and Automation (ICRA), May 29-Jun. 3, 2017, Singapore, pp. 746-753 [retrieved Jul. 21, 2017].

Shrivastava, A., et al., "Learning From Simulated and Unsupervised Images Through Adversarial Training," Dec. 22, 2016, Arxiv.org, Cornell University Library, Cornell University, Ithaca, New York, 16 pages.

"Surgery simulator," Wikipedia, The Free Dictionary, Mar. 24, 2018, <https://en.wikipedia.org/w/index.php?title=Surgery_simulator&oldid=832275506> [retrieved Jun. 17, 2019], 3 pages.

Aerial Informatics and Robotics Platform—Microsoft Research, Retrieved from Internet <https://www.microsoft.com/en-us/research/project/aerial-informatics-robotics-platform/> Mar. 1, 2018, 7 pages.

Intuitive Surgical—da Vinci Surgical System—Skills Simulator, Retrieved from Internet <https://www.intuitive.com/en-us/products-and-services/da-vinci/education> Mar. 1, 2018, 3 pages.

Shrivastava, A. et al., "Learning from Simulated and Unsupervised Images through Adversarial Training", arXiv:1612.07828 [cs.CV], Dec. 22, 2016, 16 pages.

MSim, Realistic and Life-Like Simulation for all Core Robotic Skills, Retrieved from Internet <https://mimicsimulation.com/products/technology/msim/> Mar. 1, 2018, 8 pages.

Bartyzal, R., "Multi-Label Image Classification with Inception Net", Retrieved from Internet <https://towardsdatascience.com/multi-label-image-classification-with-inception-net-cbb2ee538e30> Mar. 9, 2019, 11 pages.

"Minimally Invasive Surgery Simulation", SenseGraphics, Retrieved from Internet <https://sensegraphics.com/simulation/minimally-invasive-surgery-simulation/> Mar. 1, 2018, 4 pages.

"Simulators", 3D Systems, Retrieved from Internet <https://simbionix.com/simulators/> Mar. 1, 2018, 2 pages.

"Surgical Simulation Training Solutions", CAE Healthcare, Retrieved from Internet <https://caehealthcare.com/surgical-simulation/> Mar. 1, 2018, 8 pages.

"Virtual Simulator for Robots", NVIDIA, <https://www.nvidia.com/en-us/deep-learning-ai/industries/robotics/> Mar. 1, 2018, 6 pages.

* cited by examiner

SURGICAL SIMULATOR PROVIDING LABELED DATA

CROSS-REFERENCE TO RELATED APPLICATIONS

This application is a continuation of U.S. application Ser. No. 16/373,261, filed Apr. 2, 2019, which claims the benefit of U.S. Provisional Application No. 62/660,726, filed Apr. 20, 2018, all of which contents are hereby incorporated by reference.

TECHNICAL FIELD

This disclosure relates generally to surgical simulators, and in particular but not exclusively, relates to robot-assisted surgical simulators.

BACKGROUND INFORMATION

Robotic or computer assisted surgery uses robotic systems to aid in surgical procedures. Robotic surgery was developed as a way to overcome limitations (e.g., spatial constraints associated with a surgeon's hands, inherent shakiness of human movements, and inconsistency in human work product, etc.) of pre-existing surgical procedures. In recent years, the field has advanced greatly to limit the size of incisions, and reduce patient recovery time.

In the case of open surgery, autonomous instruments may replace traditional tools to perform surgical motions. Feedback-controlled motions may allow for smoother surgical steps than those performed by humans. For example, using a surgical robot for a step such as rib spreading may result in less damage to the patient's tissue than if the step were performed by a surgeon's hand.

Even with robotic or computer assisted surgery, complications during surgery may occur. The surgeon, for example, may incorrectly identify an anatomical structure due to the sometimes limited view of a surgical site. In another example, the surgeon may inadvertently nick or cut the anatomical structure with the instrument. Furthermore, the mechanical operation of the robotic system, or even the operation of traditional surgical tools, may require a significant degree of training to ensure competency. For example, resident general surgeons are often required to perform at least 850 operative procedures during residency.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of a system and method for a surgical simulator that automatically provides machine learning training data are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Applying machine learning to surgical data to help automatically understand, evaluate, organize, and enhance surgical data is of great interest and a new area of artificial intelligence. However, the process of applying machine learning to surgical data may include several bottlenecks or drawbacks. For example, annotations may typically come from surgeons or other trained medical professionals, which make them more difficult and costly to come by. Certain annotation tasks, such as region of interest markings and pixel-level semantic segmentation are very labor intensive and costly to produce. Furthermore, for much of the surgical data, the exact ground truth data, such as precise object position, is not known. Disclosed herein, are embodiments of a surgical simulator which automatically generates a large portion of labeled training data. This may result in freeing surgeons to only label data that requires higher level domain specific knowledge and reduce the overall cost of generating the magnitude of training data necessary for artificial intelligence applications.

In some embodiments, an enhanced surgical simulator which generates labeled data for a machine learning model in a systematic and automated way is described. The surgical simulator receives an input or defines a surgical scenario. The surgical scenario may correspond to a specific surgical procedure and may have an associated task or training scenario (e.g., instrument segmentation, surgical instrument tracking, surgical complications such as bleeding, etc.) for the machine learning model to learn how to predict. The surgical simulator then simulates the scenario and records a representative simulated surgical video. The surgical simulator also records, associates, annotates, and/or labels simulated ground truth data (e.g., telemetry, position, motion, acceleration, labels) with the corresponding simulated surgical video. The simulated ground truth data, along with the simulated surgical video can then be used to pre-train the machine learning model to identify features corresponding to the associated task.

The machine learning model can further be tuned (e.g., trained) with real world data (e.g., non-simulated surgical videos). The fine-tuning of the machine learning model can be further utilized as feedback for how to improve the simulation and to provide higher quality and more targeted data. This forms an iterative loop to improve both the simulation from the surgical simulator and the training of the machine learning model. In one embodiment, the surgical simulator is used to record surgical instrument simulation data to pre-train the machine learning model for tools tracking and segmentation. The real surgical data (e.g., from the non-simulated surgical videos) with annotations can then be utilized to do fine-tuning and additional training of the machine learning model to adapt the machine learning model to the real world.

The simulated ground truth data is known because it corresponds to simulated elements generated by the surgical simulator. For example, in the simulation, the 3D CAD models of the objects and the manipulations done on them are known. Everything being rendered in the virtual/simulated environment is knowable. This includes the surgical instruments being used, where (e.g., exact position in 3D space) they are in the space being rendered, the objects they are interacting with, their exact shapes and boundaries, and the events that are happening. The simulation is then recorded as a simulated surgical video and associated with the simulated ground truth data. This simulation can be done on a surgical scenario basis (e.g., individual surgical techniques, surgical steps, and/or surgical procedures). From the simulated ground truth data, features of the simulated surgical video may be labeled or annotated. The features may include surgical instrument presence, surgical instrument segmentation, surgical instrument tracking, telemetry of the surgical instrument, anatomy being worked on, exact morphology of the anatomy, events that are happening (e.g., smoke, bleeding, cleaning, coagulation, etc.), and distances between surgical tools and the anatomy. In some embodiments, a deep neural network may be utilized to simulate physics and surface texture of the anatomy (e.g., liver) for training in surgical complications such as bleeding or smoking events.

Advantageously, the surgical simulator provides automated machine learning data gathering. Certain tasks or features (e.g., pixel level object segmentation) may be accomplished with reduced economic and labor costs. This process can be automated in the simulated environment to produce large amounts of labeled training data at an individual image frame level. This automated data generation may thus free medical practitioners to annotate other higher level features that may require their medical expertise (e.g., specific surgical technique being applied, workflow, surgery specific steps, etc.). Additionally, this automated process may generate more data in rare surgical scenarios such as surgical complications what would normally be scarcely available in a non-simulated environment. For example, in some circumstances there may be a limited supply of real surgical videos representing one or more surgical complications. In some embodiments, the surgical simulator may provide simulated surgical videos corresponding to the one or more surgical complications. Thus, the surgical simulator, in some circumstances, may supplement the potential lack of real surgical videos.

Figure 1:
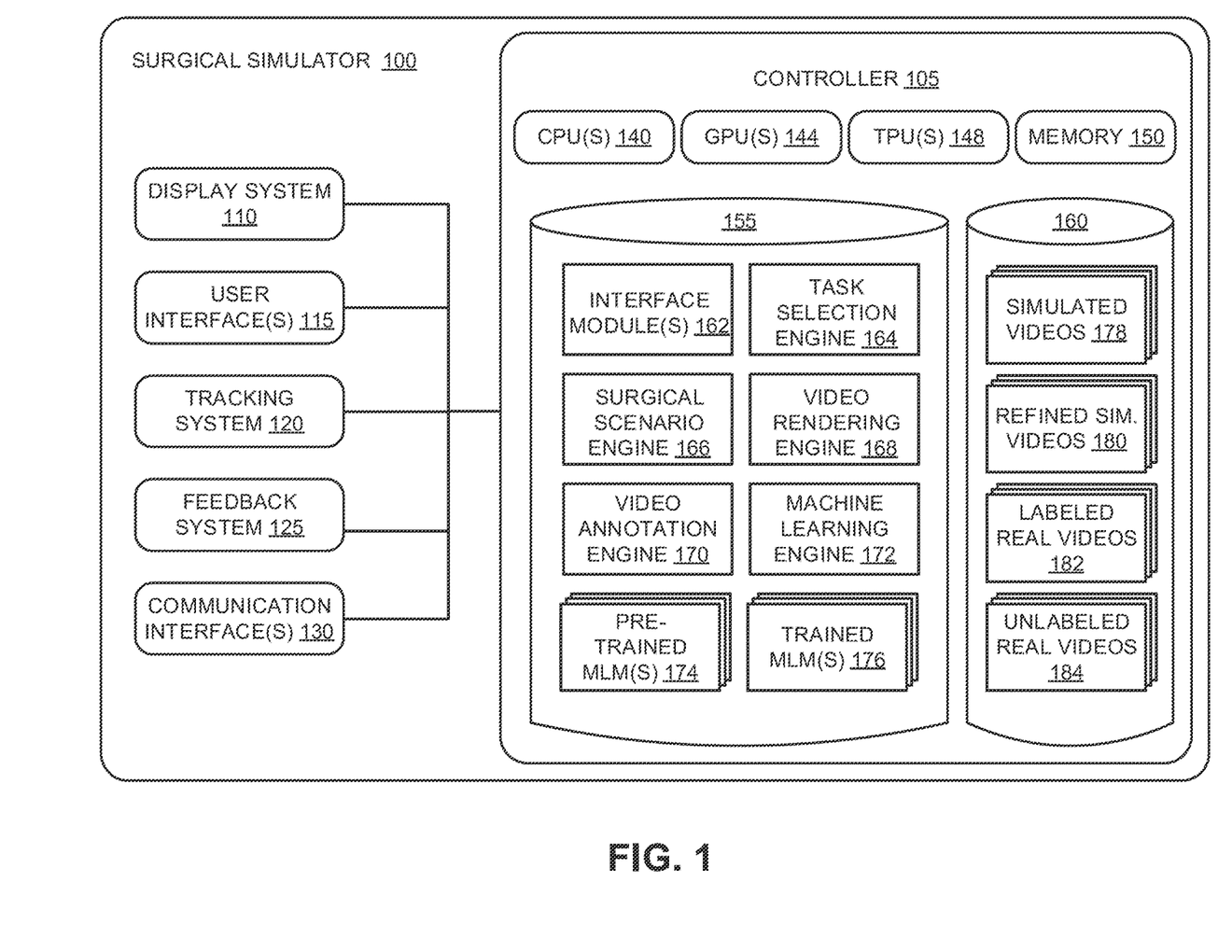
FIG. 1 illustrates a system for a surgical simulator adapted to simulate a surgical scenario and automatically generate labeled surgical data for a machine learning model, in accordance with an embodiment of the present disclosure.

FIG. 1 is an example surgical simulator 100 adapted to simulate a surgical scenario, in accordance with an embodiment of the disclosure. System 100 includes controller 105, display system 110, user interfaces 115, tracking system 120, feedback system 125, and communication interfaces 130. Controller 105 includes one or more central processing units (CPU) 140, one or more graphic processing units (GPU) 144, one or more tensor processing units (TPU) 148, memory 150, data store 155, and data store 160 coupled to one another (e.g., via a communication bus). The data store 155 includes one or more interface modules 162, a task selection engine 164, a surgical scenario engine 166, a video rendering engine 168, a video annotation engine 170, a machine learning engine 172, one or more pre-trained machine learning models (MLM) 174, and one or more trained MLMs 176. The data store 160 may correspond to a surgical video database and include simulated surgical videos 178, refined simulated surgical videos 180, labeled real surgical videos 182, and unlabeled real surgical videos 184. It should be appreciated that one or more of the components illustrated in FIG. 1 are optional and need not be present in all embodiments.

As illustrated, the display system 110, the user interfaces 115, the tracking system 120, the feedback system 125, and the communication interfaces 130 are coupled to one another and the controller 105. The controller 105 orchestrates the operation of the surgical simulator 100 in response to one or more inputs from a user (e.g., a medical practitioner) of the surgical simulator 100 and instructions stored within the memory 150 or the data store 155. The display system 110 may include one or more displays (e.g., liquid crystal display, organic light emitting diode display, and the like) to display surgical videos (e.g., the simulated surgical videos 178, the refined simulated surgical videos 180, the labeled real surgical videos 182, and the unlabeled real surgical videos 184 of the data store 160) to the user. In the same or other embodiments, the display system 110 may show the simulation to the user in real time or near real time as the simulation is being generated in order to allow the user to perform simulated actions within the simulation of the surgical scenario (e.g., creating an incision, excising a tumor, suturing, and the like).

The user interfaces 115 may include interface devices that may be physically manipulated by the user which the surgical simulator 100 correlates as a simulated action with a simulated surgical instrument during the simulation. For example, the interface devices may include a touchscreen, a game pad, a mouse, a keyboard, a track pad, a surgical instrument (e.g., graspers, clamps, retractors, scalpels, scissors, staplers, endoscopes, and the like), a foot pedal, a control console, a computer screen, and the like. In some embodiments, the surgical simulator 100 may include the same or similar instruments utilized in robotic assisted surgery as interface devices to provide a realistic simulation experience. In the same or other embodiments, the interface devices may include a microphone for receiving voice commands or cameras for receiving gesture commands. The user may physically manipulate the one or more interface devices to cause a change in motion (e.g., position, orientation, velocity, acceleration) of the one or more interface devices which is then tracked by the tracking system 120.

During the simulation, the tracking system 120 records changes in the motion of the one or more interface devices and simulates a corresponding motion of the simulated surgical instrument to allow for the user to perform simulated surgical actions within the simulation. In one embodiment, the tracking system 120 may include cameras, infrared lights, one or more eye trackers, a watch, and the like to record the physical motion of the user (e.g., appendage movement, body movement, head movement, eye movement, etc.). In some embodiments, the tracking system 120 includes various sensors (e.g., one or more biometric sensors worn by the user) and cameras to record the physiological response of the user during the simulation, which may be correlated to the difficulty or importance of a particular surgical step or technique. For example, the tracking system 120 may record pulse, blood pressure, perspiration, or other physiological features. The feedback system may provide feedback (e.g., haptic motion, visual representation, audible cues, etc.) to inform the user of a surgical event (e.g., the simulated instrument contacting the anatomical region). The feedback system may include one or more speakers, displays, transducers and the like to provide the corresponding feedback.

The communication interfaces 130 are provided to facilitate intercommunication between components of the surgical simulator 100 and exterior devices. For example, the communication interfaces 130 may include known wired data buses (e.g., USB, Ethernet, etc.) and wireless interfaces (e.g., Bluetooth, WiFi, etc.). In some embodiments, one or more components of the surgical simulator 100 may be remotely located or cloud-based. In a cloud-based architecture, processing (e.g., with the CPUs 140, GPUs 144, and/or TPUs 148) may occur remotely and the results (e.g., the trained machine MLMs 176) uploaded into the local instance of the controller 105.

As illustrated in FIG. 1, the controller 105 is interconnected with the other components of the surgical simulator 100 to control and choreograph their interactions. Processors (e.g., CPUs 140, GPUs 144, TPUs 148, application specific integrated circuits, or otherwise) control the operations of the surgical simulator 100 via the execution of logic/modules/engines within data store 155 as instructions, which may be stored locally within memory 150. The modules 162-176 may be implemented as software logic (e.g., executable software code), firmware logic, hardware logic, or various combinations thereof.

The interface modules 162 control or receive inputs from the user interfaces 115 and the tracking system 120. The task selection engine 164 provides a list of tasks for the user to select (or to be automatically selected by the surgical simulator 100) for pre-training or training the machine learning model. For example, the task of instrument identification, anatomy identification, instrument segmentation, anatomy segmentation, surgical step identification, and the like may be selected via the task selection engine 164. The selected task may also closely correlate to features for the machine learning model to identify or predict. The selected task may also include identifying smoke, identifying cauterization, identifying bleeding, identifying specific surgical techniques, detecting the skill of the surgeon, interfering depth based on scale (e.g., how close the tool is to the anatomy), danger zone identification (e.g., the tool is too close to a specific anatomical region), and the like. The surgical scenario engine 166 provides a list of surgical scenarios for the user to select to be simulated (e.g., suturing an incision, excising tumors, etc.). In some embodiments, the task of the task selection engine 164 and the surgical scenario of the surgical scenario engine 166 may be closely associated with one another. In some embodiments, the surgical simulator 100 may automatically select the task based on the selection of the surgical scenario, or vice versa. In one embodiment, the surgical scenario may correspond to a low anterior resection procedure and the corresponding task may be to identify surgical steps (e.g., the anastomosis step), identify the surgical instrument (e.g., clamp, forceps, knife), and/or identify particular anatomical regions (e.g., colon).

Video rendering engine 168 generates or renders the simulation to present (e.g., via the display system 110) to the user of the surgical simulator 100 in the form of the simulated surgical video. For example, during a simulation(s), the video rendering engine 168 simultaneously records a simulated surgical video(s) based on the simulation(s). The rendering also associates various simulated ground truth data within the metadata of the simulated surgical video for training the machine learning model. The simulated ground truth data corresponds to context information of at least one of a simulated surgical instrument, simulated anatomical region, or simulated surgical tasks. For example, the exact position, orientation, acceleration, boundaries, etc. of the simulated surgical instrument is known by the surgical simulator 100. Similarly, the various simulated anatomical regions and their corresponding labels, boundaries, position (e.g. in relation to other anatomical regions and/or simulated surgical instruments) are also known by the surgical simulator 100. Further, based on the surgical scenario selected, the surgical simulator knows the type of simulated surgical procedure being performed and any corresponding simulated surgical task (e.g., suturing). This information may be specifically encoded into the simulated surgical videos as associated metadata which, in addition to the simulated surgical video, may be used for pre-training or training the machine learning model. The video rendering engine may store the simulated surgical videos within data store 160 as simulated videos 178.

In some embodiments, the video rendering engine 168 generates the simulated surgical videos via one or more trained simulation models corresponding to one or more trained machine learning models and other associated models/engines for simulation of the surgical scenario. In one embodiment, the trained simulation models may be combined with a physics model, for example, to simulate a response of the anatomical region to contact with the simulated surgical instrument.

The video annotation engine 170 may receive the simulated surgical videos from the video rendering engine 168 or the data store 160. The video annotation engine 170 then specifically prepares the simulated surgical videos for training the machine learning model by annotating features of the simulated surgical videos based, at least in part, on the simulated ground truth data. The features may correspond to at least one of segments of a surgical instrument, segments of an anatomical region, motion of the surgical instrument, surgical steps of a surgical procedure, surgical technique utilization, surgical event occurrence, separation distance between the surgical instrument and the anatomical region, and the like. For example, the simulated ground truth data may include positional information of a simulated surgical instrument, which may in turn be used by the video annotation engine 172 to annotate a portion of the simulated surgical video as corresponding to features representative of a surgical instrument (e.g., real or simulated).

Annotating the simulated surgical videos may include directly altering the data of image frames from the simulated surgical videos, adding annotated metadata, generating an overlay to be superimposed on the simulated surgical video, or otherwise. In one embodiment, the video annotation engine 170 may assign metadata to groups of image pixels from corresponding image frames of the simulated surgical videos as representing the surgical instrument (e.g. real or simulated), while other groups of image pixels may have different metadata assigned indicating the other groups of image pixels correspond to a certain anatomical region. Once annotation is complete, the video annotation engine 170 may store the simulated surgical videos (e.g., along with the associated metadata and/or labels) within the data store 160.

The machine learning engine 172 may then pre-train the machine learning model with the features annotated from the simulated surgical videos. The pre-training configures the machine learning model to probabilistically identify the features (e.g., identify segments/pixels corresponding to the surgical instrument) from unlabeled simulated videos corresponding to the surgical scenario (e.g., the lower anterior resection procedure). The machine learning model, after pre-training, may be able to determine within a certain degree of confidence whether the groups of pixels from image frames of unlabeled simulated videos (or real videos) correspond to the features.

The pre-trained machine learning models may be able to identify the features within a simulated environment (e.g., from the simulation of the surgical simulator 100), but the probabilistic accuracy may be refined further for real environments. Thus, the pre-training may provide a baseline or initial value for the machine learning model (e.g., the weight distribution of the neural network corresponding to the machine learning model). The pre-training may also provide metrics for refining the machine learning model. For example, the pre-training may indicate the amount of real data from real surgical videos for refining the machine learning model. Similarly, the pre-training may indicate which types of tasks or surgical scenarios require more training relative to other tasks or surgical scenarios. To refine the machine learning model, the machine learning model is further trained with labeled real videos (e.g., annotated videos of the surgical scenario performed by a medical practitioner in a real environment). Refining the machine learning model to identify the features based on the labeled real videos may configure the machine learning model to probabilistically identify the features from unlabeled real videos (e.g., unannotated videos of the surgical scenario performed by the medical practitioner in the real environment). This training may improve the machine learning models ability to identify the features from the real environment compared to only pre-training the machine learning model with simulated surgical videos.

In some embodiments, realism of the simulated surgical videos may be improved by inputting the simulated surgical videos into a generative adversarial network. The simulated surgical videos may be provided to a refiner neural network which increases the realism of the simulated surgical videos and outputs refined simulated videos (e.g., refined simulated videos 180 stored within the data store 160). The refiner neural network adjusts or manipulates simulated images (e.g. image frames from the simulated surgical videos 178) until a discriminator neural network determines the simulated images are comparable to unlabeled real images (e.g., image frames from the unlabeled real videos 184 stored within the data store 160) within a certain threshold. It is important to note that the annotations included in the simulated videos 178 are maintained throughout the refining process such that the refined simulated videos 180 also include the same or substantially similar annotations or labels.

It is appreciated that in some embodiments, the machine learning models that have been pre-trained or trained respectively with simulated surgical videos or real surgical videos may be saved at any time during or after the training to the data store 155 (e.g., within pre-trained MLMs 174 or trained MLMs 176). Saving the machine learning models preserves individual parameters (e.g., weight distribution coupling nodes of the neural network together) of the machine learning models. Further, in some embodiments surgical videos may be saved to data store 160 and/or outputted (e.g., displayed via the display system 110) to the user of the surgical simulator or otherwise. The surgical videos displayed may include the simulated surgical videos 178, the refined simulated surgical videos 180, the labeled real surgical videos 182, or the unlabeled real surgical videos 184.

Figure 2:
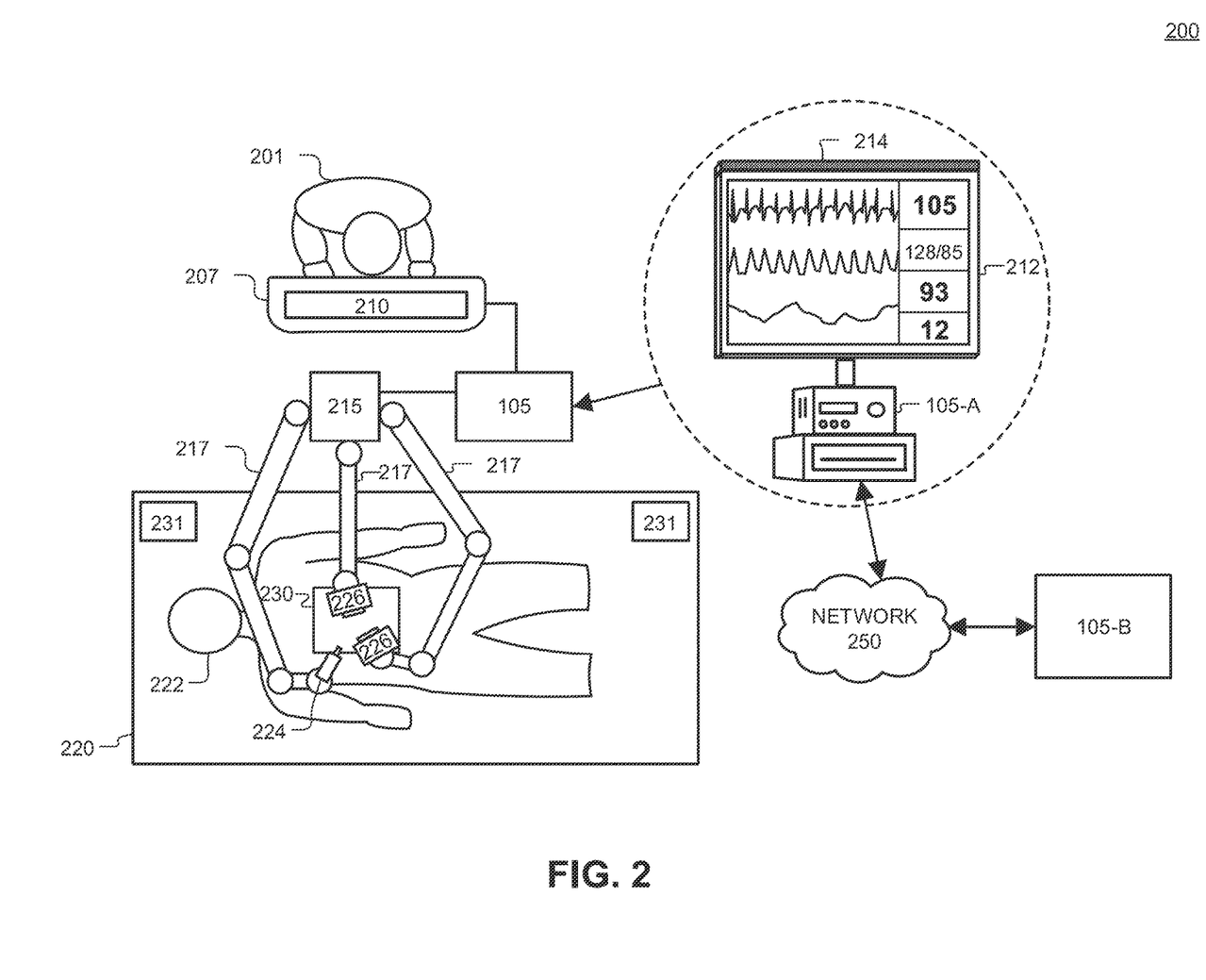
FIG. 2 illustrates a hybrid system for a surgical simulator adapted to simulate a surgical scenario and automatically generate labeled surgical data for a machine learning model, in accordance with an embodiment of the present disclosure.

FIG. 2 is an example surgical simulator 200 adapted to simulate the surgical scenario and generate annotated simulated surgical videos for a machine learning model, in accordance with an embodiment of the disclosure. Surgical simulator 200 is one possible implementation of surgical simulator 100 illustrated in FIG. 1. In the illustrated embodiment of FIG. 2, the surgical simulator 200 is a hybrid simulator that combines both virtual and real elements to generate the simulation. The surgical simulator 200 includes several input devices which may be included with or correspond to the user interfaces 115. As illustrated, these input devices include control console 207, surgical robot 215, arms 217 of the surgical robot 215, camera 224 and surgical instruments 226 coupled to a respective arm 217. The surgical simulator 200 may simulate performing a surgical procedure of a surgical scenario on a mannequin 222 disposed on a table 220. The surgical simulator 200 may also include a display 210, which may be included in the display system 110 of FIG. 1.

Furthermore, the surgical simulator 200 of FIG. 2 may also include a feedback display 212 (e.g., to display simulated vitals of the simulated patient being operated on by medical practitioner 201) and speaker 214 (e.g., to provide audio cues), which may be included with or correspond to the feedback system 125 of FIG. 1. The surgical simulator 200 may also include infrared cameras and corresponding infrared light emitting diodes 231 for movement tracking of the medical practitioner 201 which may be included in the tracking system 120 of FIG. 1. In the illustrated embodiment of FIG. 2, the controller 105 is adapted to choreograph the operations and interaction between the components of the surgical simulator 200. Components of the controller 105 may be distributed locally (e.g., the controller 105-A) or coupled to the surgical simulator 200 remotely (e.g., the controller 105-B) via network 250.

It is appreciated that the surgical simulator 200 may not necessarily be a hybrid surgical simulator. In one embodiment, the surgical simulator 200 may be a virtual simulator (e.g., software running on a computer). In other embodiments, the surgical simulator 200 may be a dedicated simulator to a specific surgical scenario (e.g., tissue deformation under pressure, wound closure/cauterizing, etc.). Thus the surgical simulator 200 may not be a full-fledged surgical simulator that simulates an entire operating room or a surgical scenario, but instead provides data regarding a specialized subset of surgical scenarios for the machine learning model. In the same or other embodiments, the surgical similar 200 may be a benchtop simulator that only simulates surgical instruments or other singular aspects of the surgical apparatus.

Figure 3:
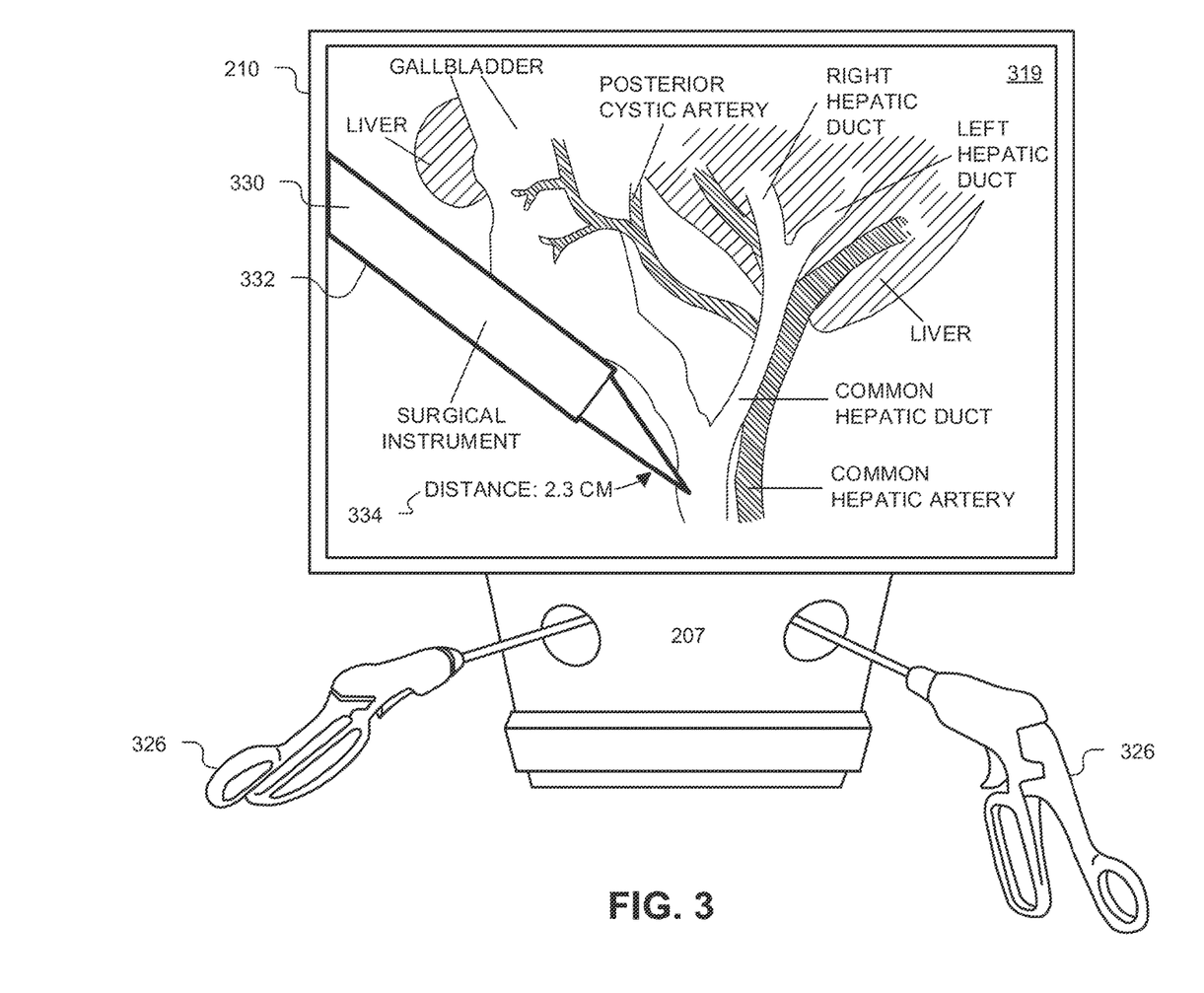
FIG. 3 illustrates an example control console and display of the surgical simulator in FIG. 2, in accordance with an embodiment of the present disclosure.

FIG. 3 illustrates an example control console 207 and display 210 of the surgical simulator 200 of FIG. 2, in accordance with an embodiment of the disclosure. As illustrated, the control console 207 includes manipulators 326, which in response to a physical action of the user control the arms 217 of the surgical robot 215 of FIG. 2. More specifically, the manipulators 326 may include triggers, buttons, levers, and the like for controlling the surgical instrument 226 of FIG. 2. This allows for the surgical simulator 200 to correlate a physical action of the user with a simulated action of the surgical simulator 200. The display 210 is outputting an image frame 319 from the simulated surgical video that has been annotated. The annotations include an overlay on the display 210 with labels identifying specific anatomical regions (e.g., liver, common hepatic duct, etc.). The image frame 319 also includes the surgical instrument 330, which may be a simulated instrument or an actual instrument controlled by manipulators 326. The surgical instrument 330 is annotated by a border 332 which identifies the segments of the surgical instrument 330 with pixel level accuracy of the simulated surgical video. The annotations may also include metadata that can be utilized to indicate the distance 334 between the surgical instrument 330 and the underlying anatomical region. This distance information may be utilized to create a depth map of the entire image frame or simulated surgical video to determine three-dimensional position of each simulated element by the surgical simulator 200.

Figure 4:
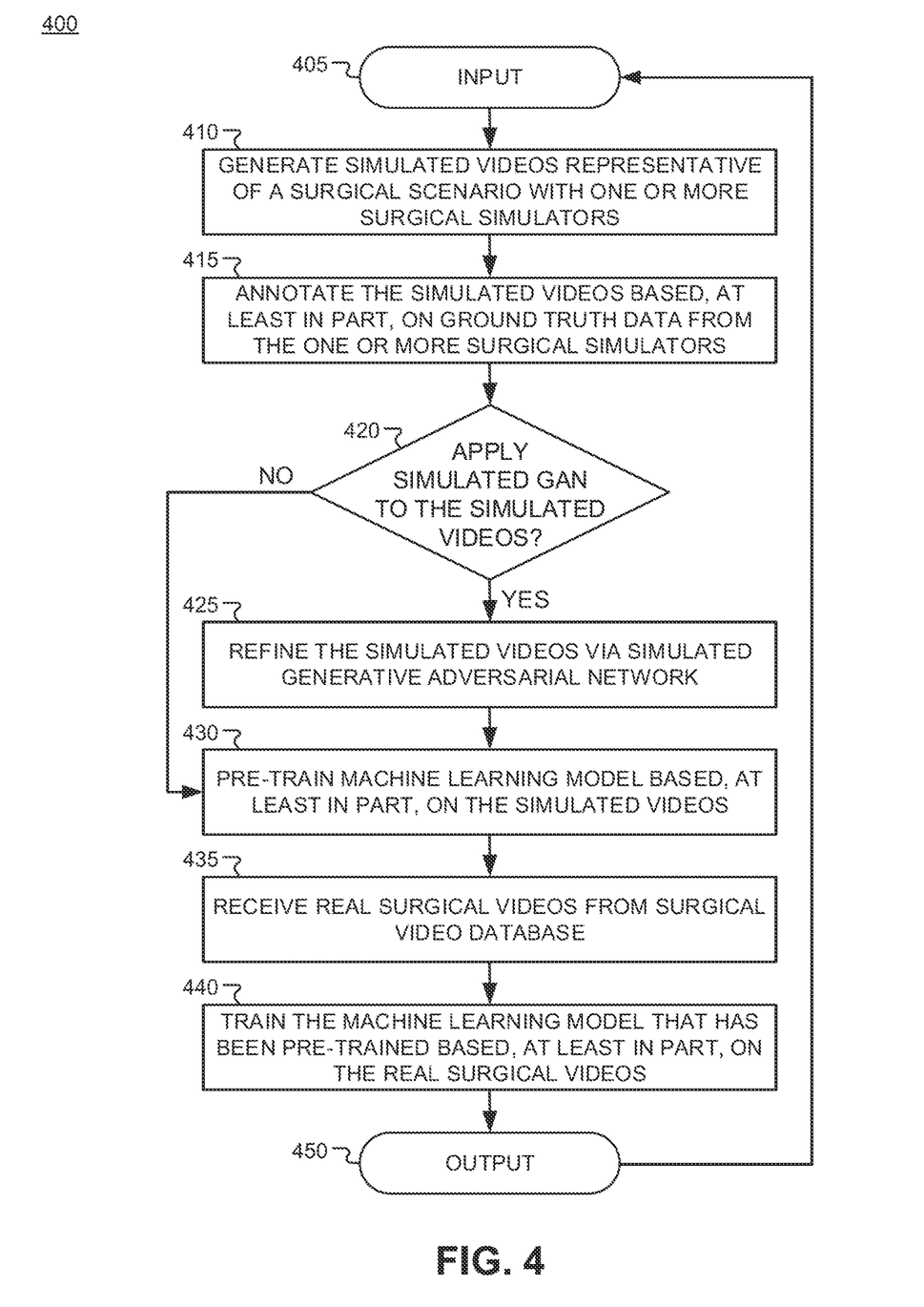
FIG. 4 illustrates a method for providing labeled training data for a machine learning model with a surgical simulator, in accordance with an embodiment of the present disclosure.

FIG. 4 illustrates a method 400 for providing labeled training data for the machine learning model with a surgical simulator, in accordance with an embodiment of the present disclosure. It is appreciated that numbered blocks 405-450 may occur in any order and even in parallel. Additionally, blocks may be added to, or removed from, method 400 in accordance with the teachings of the present disclosure.

Block 405 illustrates receiving an input (e.g., from a user or from instructions stored within the surgical simulator) to simulate a surgical scenario (e.g., lower anterior resection procedure) associated with a task (e.g., surgical instrument segmentation) to be learned via a machine learning model.

Block 410 shows generating, with the surgical simulator, simulated surgical videos each representative of a simulation of the surgical scenario. Generating the simulated surgical videos may include associating, with the surgical simulator, simulated ground truth data from the simulation. The simulated ground truth data corresponds to context information of at least one of a simulated surgical instrument, simulated anatomical region, or simulated surgical task. Since the surgical simulator is simulating the surgical scenario, exact position, orientation, acceleration, and the like of any simulated element (e.g., surgical instrument, anatomical region) is known.

In some embodiments, the 3D CAD models of the simulated elements (e.g., surgical instrument, anatomical region) and the manipulations done on or by them is known. Everything being rendered in the virtual environment during the simulation is known, the surgical tools being used, where (the exact positions) they are in the space being rendered, the objects they are interacting with, their exact shapes and boundaries, and the events that are happening. The simulated ground truth data may incorporate some or all of this context information as metadata for the simulated surgical videos. More specifically, in some embodiments, the context information of each of the simulated surgical videos includes at least one of three-dimensional spatial boundaries of the simulated surgical instrument, three-dimensional spatial boundaries of the simulated anatomical region, motion of the simulated surgical instrument, separation distance between the simulated surgical instrument and the simulated anatomical region, orientation of the simulated surgical instrument, temporal boundaries (e.g., duration and associated image frames) of one or more surgical steps of the simulated surgical task from the surgical scenario, temporal boundaries of a simulated surgical complication (e.g., bleeding, smoke, etc.), or spatial/temporal boundaries of the simulated surgical complication.

Block 415 illustrates annotating, with the surgical simulator, features of the simulated surgical videos based, at least in part, on the simulated ground truth data for training a machine learning model. Annotation may involve manipulating the image data of the simulated surgical video, assigning metadata to pixels of image frames from the simulated surgical video, and the like. In one embodiment, the features annotated with the surgical simulator include at least one of segments of a surgical instrument, segments of an anatomical region, motion of the surgical instrument, surgical steps of a surgical procedure, surgical technique utilization, surgical event occurrence, or separation distance between the surgical instrument and the anatomical region. The features may be represented to the user of the surgical simulator viewing the simulation via an overlay which labels, highlights, or otherwise indicates the features of the simulated surgical video.

Block 420 shows determining whether to apply a simulated generative adversarial network (SimGAN) to the simulated surgical videos to increase realism of the simulation. If the level of realism is determined to be within a certain threshold block 420 proceeds to block 430 and does not apply the SimGAN technique to the simulated surgical videos. However, in some embodiments, it may be preferable that image frames from the simulated surgical video have a more realistic appearance to prevent over-fitting of the machine learning model. In other words, SimGAN may prevent the machine learning model from being too specific to the simulation. This may reduce the accuracy of the machine learning model in classifying features of real videos relative to features of simulated videos. In some embodiments, a collection of real surgical videos that are categorized and closely related to the surgical scenario that has been simulated are obtained (e.g., from the surgical video database). The SimGAN process then utilizes the collection of real surgical videos to make the corresponding simulated surgical video more closely related or representative of the targeted surgical scenario. This may prevent the machine learning model from learning features that are too specific to the simulated surgical video that may not be present in a corresponding real surgical video.

Block 425 illustrates refining the simulated videos by a SimGAN technique. This includes providing, to a refiner neural network, simulated images from the simulated surgical videos. The refiner neural network then manipulates the image data of the simulated images to form refined surgical videos based, at least in part, on the simulated surgical videos. The features annotated from the simulated surgical videos are maintained and thus included with the refined surgical videos. The refiner neural network is trained based on an adversarial loss to a discriminator neural network which compares unlabeled real images (e.g., representative of the surgical scenario in a real environment) to the simulated images. In other words, the refiner neural network adjusts the simulated images until the discriminator neural network determines that the simulated images are comparable to the unlabeled real images within a first threshold.

Block 430 shows pre-training the machine learning model with the features annotated from the simulated surgical videos. The pre-training configures the machine learning model to probabilistically identify the features from unlabeled videos corresponding to the surgical scenario. After the pre-training the machine learning model may be able to identify the features from simulated surgical videos, but the accuracy of identifying features from real surgical videos may be lacking. For example, only training on the simulated surgical videos may, in some embodiments, lead to overfitting to the simulated data. Thus, in some embodiments pre-training may provide an initialization point for the weight distribution of the machine learning model to identify the features of real surgical videos.

Block 435 illustrates receiving real surgical videos from a surgical video database. The real surgical videos are representative of the surgical scenario in the real environment (e.g., not simulated) being performed by a medical practitioner. The real surgical videos are labeled/annotated for training the machine learning model. In other words, the real surgical videos may be utilized to refine the machine learning model to identify features of unlabeled real surgical videos.

Block 440 shows training the machine learning model (previously pre-trained on the simulated surgical videos) on the real surgical videos. The training configures the machine learning model to probabilistically identify the features from the unlabeled real videos corresponding to the surgical scenario in a real environment (e.g., not simulated). Therefore, the training refines, adjusts, or modifies the weight distribution of the machine learning model such that the accuracy of identifying the features of unlabeled real surgical videos is improved relative to a machine learning model trained only on simulated surgical videos.

Block 450 illustrates an output of the surgical simulator. The output may include the pre-trained machine learning model, the trained machine learning model, or other aspects of the method 400. Furthermore, the output may include labeled real surgical videos annotated with the trained machine learning model. In some embodiments, the unlabeled real videos are received from the surgical video database. The unlabeled real videos are input into the machine learning model, which identifies the features of the unlabeled real videos. Subsequently, now that the features have been identified, the surgical simulator may annotate the unlabeled videos by labeling (e.g., highlight, label, include metadata, etc.) the features. The surgical simulator may further display annotated surgical videos corresponding to the unlabeled real videos with the features identified by the trained machine learning model. The annotations may be illustrated by superimposing markers or identifiers on top of the corresponding regions of the unlabeled real videos.

Figure 5A:
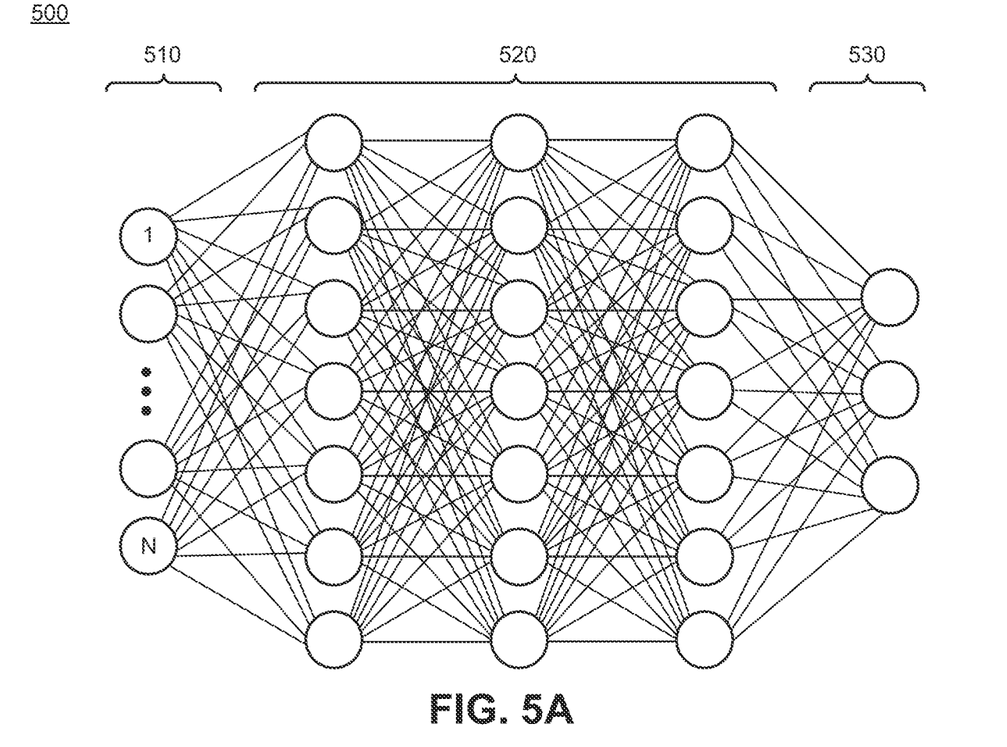
FIG. 5A illustrates an example machine learning model with a feed-forward deep neural network, in accordance with an embodiment of the present disclosure.

FIG. 5A illustrates an example machine learning model 500 with a feed-forward deep neural network, in accordance with an embodiment of the present disclosure. Machine learning model 500 includes an input layer 510, an output layer 530 and multiple hidden layers 530 disposed between the input layer 510 and the output layer 530. The number of nodes in each of the input layer 510, hidden layers 520, and output 530 is dependent on the particular surgical scenario and feature being predicted by the machine learning model 500, among other things. In some embodiments, the number of input nodes is related to the overall resolution of the simulated surgical videos, such that each pixel or groups of pixels have a corresponding input node. Similarly, the number of output nodes may be dictated by the feature or features being identified by the machine learning model. The weight distribution for the connections between nodes is not illustrated, but it is appreciated that the specific values are highly dependent on the training or pre-training method, the number of training iterations (e.g., number of training samples) performed, to name a few.

It is appreciated that the type of neural network utilized for the machine learning model 500 is highly configurable and dependent on the inputs and the feature being predicted. Thus, in some embodiments, the machine learning model 500 may utilize radial basis function neural network, a Kohonen self-organizing neural network, a recurrent neural network such as long term short term memory, a convolution neural network, a modular neural network, or other types of neural networks as known by one of ordinary skill in the art.

Figure 5B:
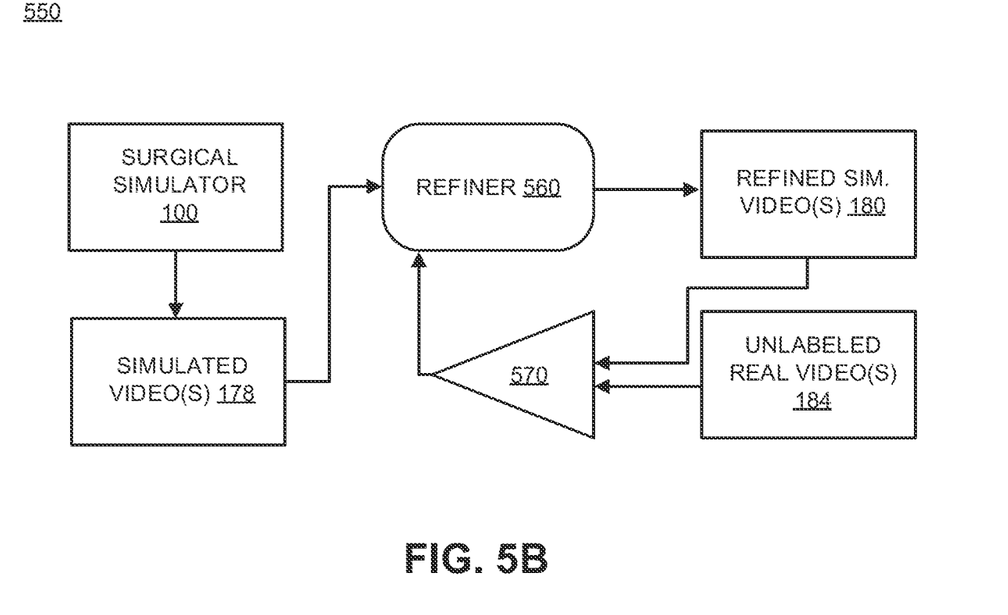
FIG. 5B illustrates a simulated generative adversarial network for refining simulated surgical videos, in accordance with an embodiment of the present disclosure.

FIG. 5B illustrates a simulated generative adversarial network (SimGAN) 550 for refining the simulated surgical videos, in accordance with an embodiment of the present disclosure. The SimGAN 550 includes the surgical simulator 100, the simulated surgical videos 178, the refined simulated surgical videos 180, the unlabeled real surgical videos 184, a refiner neural network 560, and a discriminator neural network 570. The refiner neural network 560 and the discriminator neural network 570 may be fully convolutional neural networks.

As illustrated, the refiner neural network 560 receives simulated surgical images from the simulated videos 178 generated by the surgical simulator 100. The refiner neural network 560 attempts to add realism to the simulated surgical images. To do this, the refiner neural network 560 is trained based on an adversarial loss from the discriminator neural network 570 and a self-regularization loss. The discriminator neural network 570 compares the refined surgical images of the refined simulated videos 180 output by the refiner neural network 560 to unlabeled real surgical images from unlabeled real surgical videos 184. If the discriminator neural network 570 is able to determine that the refined surgical images are not comparable to the unlabeled real surgical images within a certain threshold, then the discriminator neural network 570 issues an adversarial loss to the refiner neural network 560. The refiner neural network 560 then adjusts the model for generating refined surgical images until the discriminator neural network 570 can no longer tell the difference between the unlabeled real surgical images and the refined surgical images to within said threshold.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise. It is appreciated that terms like "a surgical robot" or "robot-assisted surgery" may include any system that aids or assists in surgery (e.g., a virtual assistant), and does not actually have to perform the surgery or have moving parts.

Some portions of the detailed description are presented in terms of algorithms and symbolic representations of operations on data bits within a computer memory. These algorithmic descriptions and representations are used by those skilled in the data processing arts to effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "generating", "receiving", "controlling", "preventing", "tracking", "enabling", "providing", "associating", "annotating", "pre-training", "training", "identifying", "refining", or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission, or display devices.

Embodiments described herein relate to an apparatus for performing the operations herein. This apparatus may be specially constructed for the specified purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

The algorithms and displays presented herein are not inherently related to any particular computer or other apparatus. Various general purpose systems may be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

A tangible machine-readable storage medium includes any mechanism that provides (i.e., stores) information in a non-transitory form accessible by a machine or controller (e.g., a computer, network device, personal digital assistant, manufacturing tool, any device with a set of one or more processors, general-purpose processor configured by firmware/software, programmable gate array, or application specific integrated circuit, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method comprising:
   generating, with a surgical simulator, simulated surgical videos each representative of a simulation of a surgical scenario;
   associating simulated ground truth data from the simulation with the simulated surgical videos, wherein the simulated ground truth data corresponds to context information of at least one of a simulated surgical instrument, a simulated anatomical region, or a simulated surgical task simulated by the surgical simulator;
   annotating features of the simulated surgical videos based, at least in part, on the simulated ground truth data to generate annotated training data for training a machine learning model;
   pre-training the machine learning model with the annotated training data to probabilistically identify the features:
   providing, to a refiner neural network, simulated images from the simulated surgical videos before the pre-training;
   refining the simulated surgical videos with the refiner neural network, wherein the refiner neural network adjusts the simulated images until a discriminator neural network determines the simulated images are comparable to unlabeled real images within a first threshold, wherein the features annotated from the simulated surgical videos are included after the refining, and wherein the unlabeled real images are representative of the surgical scenario in a real environment;
   receiving unlabeled real videos from a surgical video database, each of the unlabeled real videos representative of the surgical scenario;
   identifying the features from the unlabeled real videos with the machine learning model trained to probabilistically identify the features from the unlabeled real videos, wherein the features include at least one of a separation distance between a surgical instrument and an anatomical region, temporal boundaries of a surgical complication, or spatial boundaries of the surgical complication; and
   annotating the unlabeled real videos with the machine learning model by labeling the features of the unlabeled real videos identified by the machine learning model.

2. The method of claim 1, further comprising:
   receiving, from the surgical video database, labeled real surgical videos, each representative of the surgical scenario in the real environment, and wherein the labeled real surgical videos include the features annotated for the machine learning model; and
   after pre-training the machine learning model with the simulated surgical videos, training the machine learning model with the labeled real surgical videos to train the machine learning model to probabilistically identify the features from the unlabeled real videos.

3. The method of claim 1, wherein the context information for each of the simulated surgical videos includes at least one of three-dimensional spatial boundaries of the simulated surgical instrument, three-dimensional spatial boundaries of the simulated anatomical region, motion of the simulated surgical instrument, separation distance between the simulated surgical instrument and the simulated anatomical region, orientation of the simulated surgical instrument, temporal boundaries of one or more surgical steps of the simulated surgical task from the surgical scenario, temporal boundaries of a simulated surgical complication, or spatial boundaries of the simulated surgical complication.

4. The method of claim 1, further comprising:
rendering markers or identifiers superimposed on top of a corresponding one of the unlabeled real videos to generate annotated surgical videos.

5. The method of claim 1, further comprising:
displaying annotated surgical videos corresponding to the unlabeled real videos with the features annotated by the machine learning model superimposed on a corresponding one of the unlabeled real videos.

6. The method of claim 1, wherein the machine learning model includes at least one of a radial basis function neural network, a Kohonen self-organizing neural network, a recurrent neural network, a convolution neural network, or a modular neural network.

7. A non-transitory computer-readable storage medium having stored thereon instructions which, when executed by one or more processing units, cause the one or more processing units to perform operations comprising:
generating, with a surgical simulator, simulated surgical videos each representative of a simulation of a surgical scenario;
associating simulated ground truth data from the simulation with the simulated surgical videos, wherein the simulated ground truth data corresponds to context information of at least one of a simulated surgical instrument, a simulated anatomical region, or a simulated surgical task simulated by the surgical simulator;
annotating features of the simulated surgical videos based, at least in part, on the simulated ground truth data to generate annotated training data for training a machine learning model;
pre-training the machine learning model with the annotated training data to probabilistically identify the features;
receiving, from a surgical video database, labeled real surgical videos, each representative of the surgical scenario in a real environment, and wherein the labeled real surgical videos include the features annotated for the machine learning model; and
after the pre-training the machine learning model with the simulated surgical videos, training the machine learning model with the labeled real surgical videos to train the machine learning model to probabilistically identify the features from unlabeled real videos;
receiving the unlabeled real videos from the surgical video database, each of the unlabeled real videos representative of the surgical scenario;
identifying the features from the unlabeled real videos with the machine learning model trained to probabilistically identify the features from the unlabeled real videos, wherein the features include at least one of a separation distance between a surgical instrument and an anatomical region, temporal boundaries of a surgical complication, or spatial boundaries of the surgical complication; and
annotating the unlabeled real videos with the machine learning model by labeling the features of the unlabeled real videos identified by the machine learning model.

8. The non-transitory computer-readable medium of claim 7, wherein the instructions, which when executed by the one or more processing units, cause the one or more processing units to perform further operations comprising:
providing, to a refiner neural network, simulated images from the simulated surgical videos before the pre-training; and
refining the simulated surgical videos with the refiner neural network, wherein the refiner neural network adjusts the simulated images until a discriminator neural network determines the simulated images are comparable to unlabeled real images within a first threshold, wherein the features annotated from the simulated surgical videos are included after the refining, and wherein the unlabeled real images are representative of the surgical scenario in the real environment.

9. The non-transitory computer-readable medium of claim 7, wherein the context information for each of the simulated surgical videos includes at least one of three-dimensional spatial boundaries of the simulated surgical instrument, three-dimensional spatial boundaries of the simulated anatomical region, motion of the simulated surgical instrument, separation distance between the simulated surgical instrument and the simulated anatomical region, orientation of the simulated surgical instrument, temporal boundaries of one or more surgical steps of the simulated surgical task from the surgical scenario, temporal boundaries of a simulated surgical complication, or spatial boundaries of the simulated surgical complication.

10. The non-transitory computer-readable medium of claim 7, wherein the instructions, which when executed by the one or more processing units, cause the one or more processing units to perform further operations comprising rendering markers or identifiers superimposed on top of a corresponding one of the unlabeled real videos to generate annotated surgical videos.

11. The non-transitory computer-readable medium of claim 7, wherein the instructions, which when executed by the one or more processing units, cause the one or more processing units to perform further operations comprising displaying annotated surgical videos corresponding to the unlabeled real videos with the features annotated by the machine learning model superimposed on a corresponding one of the unlabeled real videos.

12. The non-transitory computer-readable medium of claim 7, wherein the machine learning model includes at least one of a radial basis function neural network, a Kohonen self-organizing neural network, a recurrent neural network, a convolution neural network, or a modular neural network.

13. A surgical simulator for simulating a surgical scenario, the surgical simulator comprising:
a display system adapted to show simulated surgical videos to a user of the surgical simulator;
a user interface adapted to correlate a physical action of the user with a simulated action of the surgical simulator;
a controller including one or more processors coupled to memory, the display system, and the user interface, wherein the memory stores instructions that when executed by the one or more processors cause the surgical simulator to perform operations including:
generating the simulated surgical videos, each representative of a simulation of the surgical scenario;
associating simulated ground truth data from the simulation with the simulated surgical videos, wherein the simulated ground truth data corresponds to context information of at least one of a surgical instrument, a anatomical region, a surgical task, or a surgical action simulated by the surgical simulator;

annotating features of the simulated surgical videos based, at least in part, on the simulated ground truth data to generate annotated training data for training a machine learning model to probabilistically identify the features from at least one of unlabeled simulated videos or unlabeled real videos corresponding to the surgical scenario, wherein the features include at least one of a separation distance between the surgical instrument and the anatomical region, temporal boundaries of a surgical complication, or spatial boundaries of the surgical complication;

pre-training the machine learning model with the annotated training data;

receiving, from a surgical video database, real surgical videos representative of the surgical scenario, wherein the real surgical videos include the features annotated for the machine learning model; and after the pre-training, training the machine learning model with the real surgical videos, wherein the training configures the machine learning model to probabilistically identify the features from the unlabeled real videos corresponding to the surgical scenario.

* * * * *

UNITED STATES PATENT AND TRADEMARK OFFICE
CERTIFICATE OF CORRECTION

PATENT NO. : 12,283,196 B2
APPLICATION NO. : 17/552886
DATED : April 22, 2025
INVENTOR(S) : Xing Jin et al.

Page 1 of 1

It is certified that error appears in the above-identified patent and that said Letters Patent is hereby corrected as shown below:

In the Claims

| Column | Line(s) | |
| --- | --- | --- |
| 14 | 25-26 | Claim 1, delete "features:" and insert -- features; -- |

Signed and Sealed this
Eighteenth Day of November, 2025

John A. Squires
*Director of the United States Patent and Trademark Office*